United States Patent [19]
Lopes

[11] Patent Number: 5,989,558
[45] Date of Patent: Nov. 23, 1999

[54] **METHOD OF USING *ROSMARINUS OFFICINALIS* FOR TREATING VARIOUS DISEASES**

[76] Inventor: Carlos Alberto Correia Lopes, R. Carneiro Vilela 610, ap. 303, Espinheiro-Recife, PE 52050-030, Brazil

[21] Appl. No.: 08/985,494

[22] Filed: Dec. 5, 1997

[51] Int. Cl.$^6$ ...................................................... A61K 35/78
[52] U.S. Cl. ........................ 424/195.1; 514/925; 514/929
[58] Field of Search ........................ 424/195.1; 514/925, 514/929

[56] References Cited

U.S. PATENT DOCUMENTS

| | | | |
|---|---|---|---|
| 4,318,906 | 3/1982 | Llopart | 424/195.1 |
| 4,354,035 | 10/1982 | Christ et al. | 560/75 |
| 4,358,442 | 11/1982 | Wirtz-Peitz et al. | 514/76 |
| 4,638,095 | 1/1987 | Chang et al. | 568/326 |
| 4,880,621 | 11/1989 | Grollier et al. | 424/74 |
| 5,017,397 | 5/1991 | Nguyen et al. | 426/542 |
| 5,047,249 | 9/1991 | Rothman et al. | 424/195.1 |
| 5,176,913 | 1/1993 | Honerlagen et al. | 424/195.1 |
| 5,466,455 | 11/1995 | Huffstutler, Jr. et al. | 424/401 |

FOREIGN PATENT DOCUMENTS

| | | |
|---|---|---|
| 0 034 214 | 8/1981 | European Pat. Off. . |
| 8119872 | 5/1996 | Japan . |

OTHER PUBLICATIONS

Bassani, V. et al: Preparation of a low–alcohol extract of Rosmarinus officinalis using a reverse osmosis membrane (1990), XP002097008, pp. 57–63.

"Sortiments und Presiliste '97–99", 1997, Caesar & Loretz GmbH, Germany XP002097009.

"Action of the Alcoholic Extract of Rosmarinus Officinalis Leaves on Hemorrhoidal Varixies", Lecture at 3rd Meeting of Biologic Sciences Center in Oct. 1989 and published in the Magazine Brasilica Biologica, vol. 1, supplement 1, Oct. 1, 1989.

C. Chen, "Estrane Derivatives–I*", Tetrahedron, 1958, vol. 3, pp. 43–48, Pergamon Press Ltd., pp. 43–48.

Ramani et al. "Hemorheologic Approach in the Treatment of Diabetic Foot Ulcers", Angiology, v. 44, 1993, pp. 623–626.

Rubin, "Evaluation and Treatment of Dizziness", pp. 595–620.

Adler, "Assessing the Effects of Pentoxifylline (Trental) on Diabetic Neutrophic Foot Ulcers", The Journal of Foot Surgery, vol. 30, No. 3, 1991.

Hoefler et al., "Chemical Composition of Rosmarinus Officinalis", 1986, pp. 79–89.

*Primary Examiner*—Leon B. Lankford, Jr.
*Assistant Examiner*—Christopher R. Tate
*Attorney, Agent, or Firm*—Knobbe, Martens, Olson & Bear, LLP

[57] ABSTRACT

A method for treating various diseases with a dried total extract of *Rosmarinus officinalis*. The dried total extract is obtained by macerating *Rosmarinus officinalis* leaves in hydrated ethyl alcohol for a period of 10–20 days, filtering, and drying. The dried extract has been demonstrated to be highly effective in treating patients suffering from varicose and neurotrophic ulcers, inner ear disorders, and hemorrhoids, when administered orally. The dried extract has low acute and chronic toxicity in both animals and humans. There are no side effects to the treatment.

8 Claims, No Drawings

METHOD OF USING *ROSMARINUS OFFICINALIS* FOR TREATING VARIOUS DISEASES

FIELD OF THE INVENTION

This invention relates to a method of using an extract of *Rosmarinus officinalis* to treat various diseases, including varicose and neurotrophic ulcers, diseases of the inner ear, and hemorrhoids.

BACKGROUND OF THE INVENTION

Varicose ulcers are open skin sores that are caused by trauma to an area of the skin having poor blood flow. The vascular insufficiency renders the area extremely vulnerable to injury.

The trauma can be mechanical, such as a simple scratch or a laceration. This is the most common cause of varicose ulcers. Thermal trauma, from either heat or cold, can also lead to varicose ulcers. Chemicals can cause blistering, another form of trauma. Surgery is a fourth form of trauma. All of these forms of trauma to the skin can cause varicose ulcers.

The most common locations of varicose ulcers are the lower part of the legs and the feet (M. E. Levin in M. E. Levin et al., "The Diabetic Foot", 5th Edition, pages 17–59, Mosby-Year Book, Inc., 1993). Lower limbs which are affected with eczema or swelling are especially susceptible to varicose ulcers. Diabetics are more likely to have varicose ulcers than the general population.

Patients with varicose ulcers have symptoms such as burning, pain, leg discomfort while resting, walking pain, redness of the skin, and loss of hair, in addition to the open sores on the skin.

A neurotrophic ulcer is a disease of vascular origin occurring most often in patients affected with diabetes mellitus. The blood vessels of the lower extremities are affected most often, particularly the tibial and fibular arteries and their smaller branches. Patients suffering from neurotrophic ulcers have symptoms similar to patients suffering from varicose ulcers.

Several drugs, including pentoxifylline, have been used to treat varicose and neurotrophic ulcers (P. F. Adler, J. Foot Surgery, vol. 30, pages 300–303 (1991) and Ramani et al., Angiology, vol. 44, pages 623–626 (1993)). There are several disadvantages to the present drug treatments. Healing takes a long time, 90–120 days, a long period of time to suffer from open skin sores. In addition, many patients who start drug treatment of varicose and neurotrophic ulcers have to stop the treatment due to side effects or interactions with other medicines. Finally, the conventional drug treatments are not very effective in healing the ulcers.

The Adler study, referenced above, is a typical example of conventional drug treatment of skin ulcers. In this study, 12 diabetic patients affected with neurotrophic ulcers on their feet were treated with 400 mg of pentoxifylline, three times a day. Of the 12 patients, only 9 were able to complete the six month program because of side effects from the pentoxifylline. After 60 days, only 7 of the ulcers had healed. Another ulcer healed after 120 days. One was reduced in size from 4 cm to 2 cm after six months. This study illustrates that conventional drug treatment of patients suffering from varicose and neurotrophic ulcers has side effects and does not heal all of the ulcers.

Even after drug treatment, many patients must still undergo surgery to amputate the affected limb. Although overall statistics are not available, there are data on rates of amputation for diabetics. Diabetics are far more likely to suffer from neurotrophic ulcers than people who do not suffer from this disease. The global rate of amputation in diabetic patients is 15–40 times higher than for the general population. Furthermore, 50% of the patients who have a limb amputated are likely to have another amputation within the next five years. There is a clear need for a treatment for varicose and neurotrophic ulcers which can heal the ulcers in a shorter time and which has fewer side effects than traditional drug treatments.

Inner ear problems can cause body equilibrium problems such as dizziness and nausea. Such symptoms are very common. Body equilibrium disorders are the principal cause of consultation of general clinicians (W. Rubin, Modem Treatment, vol 6, page 54 (1976)). A recent study concluded that approximately 14 million people in the United States suffer from dizziness. There are other medical conditions related to the inner ear, such as poor hearing and tinnitus, or ringing in the ears.

Various drugs, including cinarizine, flunarizine, pentoxifylline, and Ginkgo biloba, have been used to treat dizziness, poor hearing, and tinnitus. All of these drugs have side effects. For example, all of the drugs cause nausea. Several have interactions with alcohol or other drugs. Several cause sleepiness. There is a need for a drug treatment for diseases of the inner ear, such as dizziness, poor hearing, and tinnitus that does not have side effects. There is a need for a rapid, effective treatment for the symptoms resulting from inner ear problems.

Hemorrhoids occur frequently in the general population. Hemorrhoids cause symptoms such as pain, burning, bleeding during defecation, and the appearance of protruding veins, particularly in the rectal area.

The normal treatment method for hemorrhoids is surgery to remove the protruding vein. The surgery can lead to difficulties such as pain and excessive bleeding. After the surgery, the patient must maintain a strict diet to minimize the chance of recurrence of the hemorrhoids. Even if the patient maintains the strict dietary regimen, the hemorrhoids can recur. There is a need for a nonsurgical treatment for hemorrhoids.

There is a need for a convenient and effective treatment for various diseases such as varicose and neurotrophic ulcers, diseases of the inner ear, and hemorrhoids. There is also a need for a treatment for these diseases that does not have the side effects of the present drug treatment methods.

*Rosmarinus officinalis* has previously been found to be a source of materials which have beneficial properties. For example, U.S. Pat. No. 4,318,906 to Llopart describes a liquid prepared from a blend of five plant oils, including an oil from *Rosmarinus officinalis*. The blend was found to be useful in treating wounds when applied to the surface of the skin. The blend was applied to an external varicose ulcer with a spray gun four to six times per day. The wound closed up after fourteen days and was completely healed after forty days. The need to spray the wound on such a frequent basis is inconvenient to the patient and could stain clothing. The healing time of forty days is a long period for the patient to suffer the symptoms of a varicose ulcer. There is a need for a more convenient and rapid method of treating varicose ulcers.

Rosmarinic acid has been isolated by extraction from *Rosmarinus officinalis* (Ricera Sci 1958, vol. 28, p 2392 to 2393 and Tetrahedron 1958, vol. 4, p 43 to 48). Extracts containing rosmarinic acid have been tested for stimulation of circulation (Deutsche Apotherker-Zeitung 1964, vol. 104 p. 287 to 289) and for antimicrobial activity (N. Z. Alimkhodzhaeva et al, Chemical Abstracts, vol. 82, 167491).

Wirtz-Peitz et al. (U.S. Pat. No. 4,358,442) prepared a rosmarinic acid-phospholipid complex which was found to have anti-inflammatory activity in rats. Isolating rosmarinic acid from plants is a complex process involving several steps, including extraction, drying, and recrystallization (U.S. Pat. No. 4,354,035). Reacting the purified rosmarinic acid with phospholipid and isolating the product further adds to the complexity and cost. There is a need for a product which can be made more conveniently and less expensively.

Extracts from rosemary leaves, stems or the like have also been used as food antioxidants. Chang et. al. isolated the active ingredient, Rosmaridiphenol, as disclosed in U.S. Pat. No. 4,638,095.

Accordingly, the objects of the present invention are to provide a method for isolating a dried total extract of *Rosmarinus officinalis* and to demonstrate its use in treating a variety of diseases, including: varicose and neurotrophic ulcers; diseases of the inner ear such as dizziness, poor hearing, and ringing in the ears; and hemorrhoids.

SUMMARY OF THE INVENTION

According to the invention, there are provided novel methods of isolating *Rosmarinus officinalis* total extract, comprising mixing *Rosmarinus officinalis* leaves with hydrated ethyl alcohol, macerating the mixture for an extended period of time, and filtering the mixture. Preferably, the extract is dried to form a dried total extract. Advantageously, the leaves are macerated for a period of 10 to 20 days. Preferably, the hydrated ethyl alcohol has a concentration of 80 to 95 percent.

According to one aspect of the invention, patients having varicose or neurotrophic ulcers can be treated with *Rosmarinus officinalis* total extract. According to another aspect, patients suffering from inner ear diseases such as dizziness, poor hearing, or ringing in the ears can be treated with the total extract. Patients suffering from hemorrhoids can be treated with the total extract in accordance with another aspect of the invention. Advantageously, the total extract is administered orally. Preferably, the extract is administered for a period of at least 10 days. According to one aspect of the invention, the total extract is dried. Advantageously, the dried total extract is administered in a dose of 100 milligrams to 1 gram per day.

Treatment of these diseases with *Rosmarinus officinalis* total extract is far more effective than conventional drug therapy. In addition, there are no side effects from the *Rosmarinus officinalis* treatment, unlike conventional drug treatment.

DETAILED DESCRIPTION OF THE PREFERRED EMBODIMENT

It has now been found that *Rosmarinus officinalis* dried total extract is an effective treatment for neurotrophic and varicose ulcers, diseases of the inner ear, and hemorrhoids. The treatment is far more effective than the prior treatment methods in all cases, and it overcomes the problems associated with the prior treatment methods. There are no side effects when treating patients with the *Rosmarinus officinalis* dried total extract. Conventional drug treatments of these diseases have a variety of side effects. The effectiveness of the extract in treating these diseases will become evident in the examples, discussed below.

The dried total extract is obtained by macerating the *Rosmarinus officinalis* leaves in ethyl alcohol, filtering, purifying, and drying. The leaves are macerated in aqueous ethyl alcohol having a concentration between 80 and 95 volume percent ethyl alcohol, preferably between 90 and 95 volume percent ethyl alcohol, and most preferably 92.8 volume percent ethyl alcohol. The leaves are macerated in the aqueous ethyl alcohol for a period of 1 to 50 days, preferably from about 10 to 30 days, and most preferably from about 10 to 20 days. The extract has low toxicity to animals and humans when administered orally. Although it is preferred to dry the extract, it can also be used as a liquid extract without drying.

Methods for administration of the extract to the patient are selected from oral administration, parenteral administration, or topical treatment. In general, oral administration is preferred. In one form of a preferred embodiment, the extract is administered orally in the form of a powder, granule, sugar coated tablet, tablet, capsule, or the like, according to conventional methods. Administration in the form of a capsule is preferred. The extract may be mixed with one or more non-toxic diluents, for example, lactose, potato starch, sodium hydrogen carbonate, sodium alginate, magnesium silicate, calcium carbonate, hydroxypropyl cellulose, synthetic aluminum silicate, cellulose and the like. Alternatively, the extract may be mixed with another active compound such as an antibiotic, an antihypertensive drug, or other drugs used for treating a variety of diseases before being administered orally.

The effective dosage of the dried extract when administered orally to a 70 kilogram adult is in the range of 1 milligram to 10 grams/day, not including any diluents or other active compounds. More preferably, the dosage is in the range of 10 milligrams to 5 grams/day. Even more preferably, the dosage is in the range of 100 milligrams to 1 gram/day. The oral dosage may either be given at one time or be divided into separate dosages at intervals of one to twelve hours.

Injectable dosages are the same as for oral administration, or may be as little as half that for oral administration. If the extract is to be injected, it may be diluted in a carrier. Suitable carriers include, but are not limited to, tween 80, water, saline solution, or DMSO (dimethyl sulfoxide).

The injected form of the extract may contain from about 0.1% to 99.99% carrier ingredients. The injection may be intravascular, intramuscular, subcutaneous, intraperitoneal, or by any other injection method.

If used externally, the *Rosmarinus officinalis* dried extract is applied in the form of a solution, suspension, ointment, salve, cream, lotion, or rectal suppository. The composition for external application may contain from about 0.05% to 99% extract, more preferably from about 5 to 50% extract. Suitable carriers include, but are not limited to, tween 80, DMSO (dimethyl sulfoxide), glycerine, methanol, ethanol, ethylene glycol, water, or saline solution. Dosages of the *Rosmarinus officinalis* extract when applied externally range from 1 milligram to 10 grams for each centimeter$^2$ of affected area used one to nine times per day, more preferably in the range of 100 milligrams to 1 gram for each centimeter$^2$ of affected area used one to five times per day.

The effectiveness of the *Rosmarinus officinalis* dried total extract in treating a variety of diseases will become clear from the examples below.

The first example describes the method of preparation of the *Rosmarinus officinalis* dried total extract.

EXAMPLE 1

Preparation of *Rosmarinus officinalis* Dried Total Extract

The *Rosmarinus officinalis* dried total extract was prepared from the plant leaves in the following manner. The leaves were washed, dried, and macerated in 92.8% ethyl alcohol for 15 days in a sealed stainless steel container, with a ratio of 150 grams of leaves to 400 milliliters of ethyl alcohol. The slurry was filtered through a 40 centimeter diameter Watman quantitative white bend filter paper in a stainless steel funnel to separate the solid components from the resins. The filtrate was filtered several more times in a Buchner funnel with the same type of filter paper until the impurities were removed. The solvent was removed with a rotary evaporator. A total of 6.48 grams of dried extract were obtained from the 150 grams of leaves.

The second example describes the acute toxicity test of *Rosmarinus officinalis* dried total extract on mice and monkeys.

EXAMPLE 2

Acute Toxicity Test of *Rosmarinus officinalis* Dried Total Extract

The acute toxicity of the *Rosmarinus officinalis* dried total extract was tested on mice and monkeys. The following types of animals were used in these tests:

1. Male three month old albinic Swiss mice, weighing 20–22 grams
2. Female three month old albinic Swiss mice, weighing 18–21 grams
3. Male callithrix jacchus monkeys, 12–16 months old, weighing 220–250 grams
4. Female callithrix jacchus monkeys, 14–18 months old, weighing 185–210 grams The *Rosmarinus officinalis* dried extract was dissolved in 10% tween 80 in distilled water. The extract was administered orally in a single dose of 200, 400, 600, 800, and 1000 milligrams/kilogram via a gastric tube. Each dose was given to 5 male mice, 5 female mice, 2 male monkeys, and 2 female monkeys. The animals were observed over the time period of 3–30 days after administration of the extract. No deaths occurred.

None of the animals exhibited any change in behavior, respiration, or locomotive ability during the treatment. There was no change in the levels of glucose, urea, creatinine, creatine phosphokinase, total cholesterol, triglycerides, bilirubin, or transaminases (SGOT-SGPT).

There were no abnormalities in the qualitative aspects of the erythrocytes or leukocytes. There were also no changes in the blood counts.

The liver, kidneys, lung, heart, intestine, and spleen were examined, and there was no sign of parenchymatous or sinusoidal lesions or any other change.

The $LD_{50}$ (50% lethal doses) were found to be as follows:

| | |
|---|---|
| Male mice | 10.6 grams/kilogram |
| Female mice | 11.2 grams/kilogram |
| Male rats | 10.8 grams/kilogram |
| Female rats | 10.9 grams/kilogram |

The *Rosmarinus officinalis* dried total extract was therefore found to have low acute toxicity in animals.

The third example describes the results of the chronic toxicity test of *Rosmarinus officinalis* dried total extract on rats and monkeys.

EXAMPLE 3

Chronic Toxicity Test of *Rosmarinus officinalis* Dried Total Extract

The chronic toxicity of *Rosmarinus officinalis* dried total extract in animals was evaluated in the following manner.

The extract was dissolved in a 10% solution of tween 80 in distilled water and administered orally in two daily doses of 150 milligrams/kilogram each (300 milligrams/kilogram/day) for 120 days.

The following animals were used:

1. Ten male albinic cepa Wistar three month old rats weighing 200–220 grams
2. Ten female albinic cepa Wistar three month old rats weighing 190–220 grams
3. Five callithrix jacchus male monkeys, 16–18 months old, weighing 220–250 grams
4. Five callithrix jacchus female monkeys, 16–18 months old, weighing 185–210 grams There was no change in the behavior of the animals during the 120 day test. The animals showed no loss of appetite or change in weight. There were no changes in the levels of glucose, urea, creatinine, total cholesterol, triglycerides, bilirubins, transaminases (SGOT-SGPT), alkaline phosphatase, total proteins, or qualitative or quantitative aspects of the erythrocytes, leukocytes, or platelets after the extract was administered.

A complete urine exam showed no abnormalities. There were no vascular malformations or hemorrhages in the eyes. There was no interference in gametogenesis or fecundation. No adverse effect was seen in the mother or offspring during pregnancy, childbirth, or postnatal development of the offspring.

Thus, the *Rosmarinus officinalis* dried total extract had low chronic toxicity in animal tests.

Example 4 describes the acute and chronic toxicity tests of *Rosmarinus officinalis* dried total extract on human subjects.

EXAMPLE 4

Acute and Chronic Toxicity Tests of *Rosmarinus officinalis* Dried Total Extract on Human Subjects Acute and chronic human toxicological tests were run as follows. A total of 16 healthy volunteers, both male and female, between the ages of 25 and 56 years were divided into two groups of 8 each.

The *Rosmarinus officinalis* dried total extract was administered orally to the human volunteers in gelatin capsules containing 150 milligrams of the extract.

Acute toxicity was determined on one group by administering three 150 milligram capsules of dried *Rosmarinus officinalis* every eight hours (450 milligrams/day) for 7 days. At this point, the following tests were done:

1. complete clinical exam;
2. electrocardiogram;
3. complete blood count including platelet counting, bleeding time, coagulation time, prothrombin time, and enzymatic activity;
4. measurement of glucose, urea, creatinine, creatine phosphokinase, triglycerides, total cholesterol, transaminases (SGOT-SGPT), bilirubins, GT gamma, sodium, potassium, magnesium, and uric acid levels.

A chronic toxicity test was done on the second group by administering 150 milligram capsules of dried *Rosmarinus officinalis* every 12 hours (300 milligrams/day) for 90 days. Complete examinations, including all of the tests done in the acute toxicity study, were performed on all of the members of the second group after 3, 7, 30, and 120 days:

No abnormalities were seen in any of the tests. The subjects showed good gastric, hepatic, and renal tolerance to the extract. There were no mutagenic, tumorigenic, or immunogenic effects. The extract did not interact with food, antacids, hypotension drugs, diuretics, cardiac drugs, etc.

There were therefore no problems observed in the acute and chronic toxicity tests in humans while administering *Rosmarinus officinalis* dried total extract.

The following examples demonstrate the effectiveness of the *Rosmarinus officinalis* dried total extract in treating various diseases. The next example discusses the results of the treatment of patients suffering from neurotrophic and varicose ulcers.

EXAMPLE 5

Treatment of Patients Having Neurotrophic and Varicose Ulcers

A total of 35 patients having varicose ulcers were treated with *Rosmarinus officinalis* dried total extract. Out of the 35 patients, 10 had diabetes, and 25 did not. All had symptoms of burning, pain and discomfort in the legs while in a resting position, leg pains while walking, pigmentation and redness of the legs, loss of hair, and ulcers on the legs and feet.

Each patient was given one capsule containing 150 milligrams of dried *Rosmarinus officinalis* dried total extract orally every eight hours (450 milligrams/day) for a period of 60 days.

Table 1 contains a list of the various symptoms and how many of the patients showed each symptom as a function of treatment time. Table 2 gives more detail on the cicatrization (healing with scarring) of the ulcers after 30, 40, and 60 days. There is a separate column in this Table summarizing the data on the diabetic patients, because ulcers in diabetic patients tend to heal more slowly than in the general population.

TABLE 1

Number of Patients Exhibiting Symptoms of Neurotrophic and Varicose Ulcers at Various Periods of Time

| Symptoms | Before Treatment No. Cases | % | 30 Days of Treatment No. Cases | % | 60 Days of Treatment No. Cases | % |
|---|---|---|---|---|---|---|
| Walking Pain | 17 | 48.6 | 0 | 0 | 0 | 0 |
| Resting Pain | 26 | 74.3 | 0 | 0 | 0 | 0 |
| Redness | 25 | 71.4 | 12 | 37.1 | 0 | 0 |
| Hair Loss | 15 | 42.9 | 0 | 0 | 0 | 0 |
| Bright Skin | 12 | 34.3 | 8 | 22.9 | 1 | 2.9 |
| Varicose Ulcer | 31 | 88.6 | 24 | 68.6 | 0 | 0 |
| Neurotrophic Ulcer | 4 | 11.4 | 4 | 11.4 | 0 | 0 |

TABLE 2

Percent Cicatrization of Ulcers at Varying Periods of Time

| Days of Treatment | % Cicatrization | No. Patients | No. Diabetics |
|---|---|---|---|
| 30 | 50 | 10 | 2 |
| 30 | 90 | 1 | 1 |
| 30 | 100 | 4 | 0 |
| 40 | 70 | 12 | 2 |
| 40 | 100 | 7 | 0 |
| 60 | 100 | 35 | 10 |

After 30 days of treatment, none of the patients had any pain, either while walking or resting. None of the patients continued to suffer hair loss, and fewer patients reported having the other symptoms (Table 1). Only 37.1% continued to suffer redness, and only 22.9% had bright skin, significantly fewer than before treatment. The ulcers had completely healed in four patients (Table 2). Three diabetic patients had periodic numbness in the lower part of their legs and in the toes. After 60 days of treatment, none of the patients showed any symptoms of varicose or neurotrophic ulcers, including the 3 diabetic patients who had reported periodic numbness after 30 days. All of the varicose and neurotrophic ulcers had healed. Only one patient showed a remaining sign of the disease, bright skin. Bright skin is considered to be a clinical sign rather than a symptom. None of the patients had any side effects during the treatment.

The treatment of the symptoms of sufferers of neurotrophic and varicose ulcers was far more rapid than for the conventional methods of treatment. Healing with conventional drugs requires 90–180 days. Treatment of neurotrophic and varicose ulcers with the *Rosmarinus officinalis* dried total extract was complete after 60 days, a reduction in time of 33–66% over treatment with conventional drugs. The success rate for the treatment with *Rosmarinus officinalis* dried extract was 100%, far higher than for conventional drugs. In addition, there are side effects with the traditional drugs, and they can interact with other medicines. In the Adler study using conventional drugs, only 75% of the patients were able to complete the treatment, due to side effects. No patient reported having any side effects during or after treatment with the *Rosmarinus officinalis* dried total extract. The *Rosmarinus officinalis* dried total extract was therefore shown to be an effective treatment for neurotrophic and varicose ulcers without the side effects of conventional drugs.

The following example describes the effectiveness of *Rosmarinus officinalis* dried total extract in treating patients affected with inner ear problems.

EXAMPLE 6

Treatment of Patients Affected with Inner Ear Problems

Forty five male and female patients who were affected with body equilibrium and auditive problems were treated with *Rosmarinus officinalis* extract. The age of the patients ranged from 23 and 72 years, and 75% had used other medications previously to treat their symptoms.

The patients were given one gelatin capsule containing 150 milligrams of *Rosmarinus officinalis* dried total extract orally every 12 hours (300 milligrams/day) for 30 days. The effects were evaluated in clinical studies. The results of the treatment are shown in Table 3.

TABLE 3

Results from Treatment of Inner Ear Problems

| Symptom | Before Treatment No. Cases | % | 30 Days of Treatment No. Cases | % |
|---|---|---|---|---|
| Dizziness | 45 | 100 | 0 | 0 |
| Poor Hearing | 45 | 100 | 6 | 13.3 |
| Tinnitus | 41 | 91 | 2 | 5 |
| Nausea | 7 | 15.5 | 0 | 0 |

The symptoms of dizziness and nausea disapeared after 30 days treatment in 100% of the patients. Tinnitus, or ringing in the ears, was alleviated in 95% of the patients.

Poor hearing was successfully treated in 86.7% of the cases. Treatment of these diseases of the inner ear with *Rosmarinus officinalis* dried total extract was highly effective.

No patient reported any side effects. Drug therapy with conventional drugs has severe side effects, including nausea, sleepiness, and interactions with other drugs. The *Rosmarinus officinalis* extract was therefore highly effective in treating these diseases of the inner ear, without the side effects of conventional drugs.

The next example describes the effectiveness of *Rosmarinus officinalis* dried total extract in treating patients suffering from hemorrhoids without the need for surgery, the conventional treatment.

EXAMPLE 7

Treatment of Patients Having Hemorrhoids

A total of 265 male and female patients with internal and external hemorrhoids in chronic and acute phases were treated with *Rosmarinus officinalis* dried total extract. The patients ranged from 12–88 years of age. All of the patients had previously used conventional medication with poor success. One capsule containing 150 milligrams of *Rosmarinus officinalis* dried total extract was orally administered to each patient every 12 hours (300 milligrams/day) for 30 days. The results of the treatment with *Rosmarinus officinalis* total extract were evaluated both by visual inspection and subjective evaluation.

The effect of the treatment on various symptoms from hemorrhoids is summarized in Table 4.

TABLE 4

Number of Patients Having Symptoms from Hemorrhoids as a Function of Treatment Time

| Symptoms | Before Treatment | | After 7 Days of Treatment | | After 15 Days of Treatment | | After 30 Days of Treatment | |
| --- | --- | --- | --- | --- | --- | --- | --- | --- |
| | No. of Cases | % | No. of Cases | % | No. of Cases | % | No. of Cases | % |
| Pain | 204 | 77 | 0 | 0 | 0 | 0 | 0 | 0 |
| Burning | 133 | 50.2 | 0 | 0 | 0 | 0 | 0 | 0 |
| Perianal Bleeding | 177 | 66.8 | 0 | 0 | 0 | 0 | 0 | 0 |
| Internal Hemorrhoids | 265 | 100 | 99 | 37.3 | 10 | 3.8 | 0 | 0 |
| External Hemorrhoids | 265 | 100 | 99 | 37.3 | 9 | 3.4 | 2 | 0.75 |

Within 7 days of starting treatment, 100% of the patients reported that the symptoms of pain, burning, and perianal bleeding had disappeared. None of these symptoms recurred during the remainder of the treatment. The hemorrhoids disappeared from 62.7% of the patients in the first 7 days.

After 15 days of treatment, the internal hemorrhoids had disappeared in 96.2% of the patients, and the external hemorrhoids in 96.6% of the patients.

After 30 days of treatment, only 2 patients, or 0.75%, had external hemorrhoids, and none had internal hemorrhoids. The therapy with *Rosmarinus officinalis* dried extract was over 99% effective in eliminating the hemorrhoids within 30 days without the need for surgery, the conventional treatment. None of the patients had any side effects. Removing the hemorrhoids surgically can have severe side effects such as infection. *Rosmarinus officinalis* dried total extract was therefore shown to be highly effective in treating patients suffering from hemorrhoids.

From the data presented, *Rosmarinus officinalis* dried total extract has been shown to be effective in treating a variety of diseases without side effects. Vascular and neurotrophic ulcers were healed within 60 days without the side effects of other drugs used previously. The treatment healed 100% of the ulcers, a far better success rate than for conventional drug therapy. The symptoms of inner ear diseases such as dizziness and nausea were cured in 30 days without the side effects of conventional drug treatment. Hemorrhoids were cured in over 99% of the cases without the need for surgery, the traditional treatment. No side effects were observed in any of the patients treated with the *Rosmarinus officinalis* dried total extract.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

What is claimed is:

1. A method of treating a patient having varicose or neurotrophic ulcers, comprising the step of orally administering to said patient a composition comprising dried *Rosmarinus officinalis* total extract in a dose of 100 milligrams to 1 gram per day, wherein the dried *Rosmarinus officinalis* total extract is prepared by macerating *Rosmarinus officinalis* leaves in aqueous ethyl alcohol to form a total extract and then driving the total extract.

2. The method of claim 1, wherein said composition is administered for a period of at least 10 days.

3. The method of claim 1, wherein the leaves are macerated for a period of 1 to 50 days.

4. The method of claim 1, wherein the leaves are macerated for a period of about 10 to 30 days.

5. The method of claim 1, wherein the leaves are macerated for a period of about 10 to 20 days.

6. The method of claim 1, wherein the aqueous ethyl alcohol has a concentration of between 80 and 95 volume percent ethyl alcohol.

7. The method of claim 1, wherein the aqueous ethyl alcohol has a concentration of between 90 and 95 volume percent ethyl alcohol.

8. The method of claim 1, wherein the aqueous ethyl alcohol has a concentration of 92.8 volume percent ethyl alcohol.

* * * * *